(12) United States Patent
Mukumoto et al.

(10) Patent No.: US 8,229,059 B2
(45) Date of Patent: Jul. 24, 2012

(54) X-RAY CT APPARATUS AND CONTROL METHOD OF X-RAY CT APPARATUS

(75) Inventors: Go Mukumoto, Nasushiobara (JP); Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 76 days.

(21) Appl. No.: 12/417,230

(22) Filed: Apr. 2, 2009

(65) Prior Publication Data

US 2009/0252286 A1    Oct. 8, 2009

(30) Foreign Application Priority Data

Apr. 4, 2008   (JP) ................... 2008-098227

(51) Int. Cl.
*G01N 23/083* (2006.01)
*H05G 1/08* (2006.01)
*H05G 1/32* (2006.01)
*H05G 1/60* (2006.01)

(52) U.S. Cl. ............... 378/4; 378/112; 378/162

(58) Field of Classification Search ............. 378/4–20, 378/111, 112, 162
See application file for complete search history.

(56) References Cited

U.S. PATENT DOCUMENTS

| | | | | |
|---|---|---|---|---|
| 6,775,352 | B2 * | 8/2004 | Toth et al. | 378/108 |
| 7,215,733 | B2 * | 5/2007 | Nabatame | 378/16 |
| 7,280,635 | B2 * | 10/2007 | Toth | 378/108 |
| 7,602,880 | B2 * | 10/2009 | Hirokawa et al. | 378/8 |
| 7,813,471 | B2 * | 10/2010 | Hirokawa et al. | 378/4 |
| 2003/0016778 | A1 * | 1/2003 | Tachizaki et al. | 378/4 |
| 2003/0076919 | A1 * | 4/2003 | Suzuki | 378/4 |
| 2005/0008115 | A1 * | 1/2005 | Tsukagoshi | 378/4 |
| 2005/0249329 | A1 * | 11/2005 | Kazama et al. | 378/16 |
| 2008/0144764 | A1 * | 6/2008 | Nishide et al. | 378/5 |
| 2009/0016484 | A1 * | 1/2009 | Wang | 378/19 |
| 2009/0309874 | A1 * | 12/2009 | Salganicoff et al. | 345/419 |
| 2010/0158336 | A1 * | 6/2010 | Motomura et al. | 382/131 |

FOREIGN PATENT DOCUMENTS

JP    2002-177261    6/2002

* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

An X-ray CT apparatus has an irradiation unit, a determination unit, and a displaying unit. The irradiation unit is configured to emit an X-ray. The determination unit determines a tube current value modulation to extend to a body axis direction in a predetermined rotation angle of the irradiation unit based on an index value to show a dispersion of CT values in a required area in a reconstructed image, and a scan condition. The displaying unit displays an image of the index value and an image of the tube current value modulation on an image used for positioning and aligns the image along the body axis direction on the image used for positioning.

10 Claims, 9 Drawing Sheets

FIG. 6B

X-RAY CT APPARATUS AND CONTROL METHOD OF X-RAY CT APPARATUS

BACKGROUND OF THE INVENTION

1. Field of the Invention

The present invention relates to an X-ray CT (computerized tomography) apparatus and a control method of an X-ray CT apparatus which can set an appropriate tube current to a different portion of a helical scan performed once by preliminarily designating an index value to show a dispersion of CT values in required area in a reconstructed image.

2. Description of the Related Art

An X-ray CT apparatus provides a sectional image of a portion to be diagnosed of a patient by performing a scan by irradiating an X-ray to the portion to be diagnosed from a plurality of directions and performing an image reconstructing process based on projected data obtained by the X-rays from respective directions passing through the portion to be diagnosed. It is necessary for an operator such as a technician and the like to make a plan in conformity with a portion to be diagnosed and a diagnosis purpose as to scan conditions and condition of the image reconstructing process prior to the scan and the like. This plan is called a scan plan. The X-ray CT apparatus generally provides a user interface environment for a scan plan performed on an operation console.

Incidentally, since a portion to be diagnosed, for example, a lung occupies almost all the portions of a breast portion, an amount of X-ray attenuation is small, whereas since many organs exist in an abdominal portion, an amount of X-ray attenuation is large. Further, since patients have a different body shape, even the same portion has a different amount of X-ray attenuation depending on the patients.

There is known a so-called "Auto mA" technology which automatically controls a tube current value applied to an X-ray tube for determining an amount of X-ray for each patient or each scan position to cope with an amount of X-ray attenuation which is different in each patient or each portion to be diagnosed. If this technology is used, since an appropriate amount of X-ray can be set in accordance with a portion to be diagnosed having a different amount of X-ray attenuation, a tomographic view having good S/N can be obtained while suppressing wasteful exposure. Further, this technology has an advantage in that it contributes to prolong the life of the X-ray tube. Whether an "Auto mA" function is turned ON or OFF can be designated when the scan plan is made. When the "Auto mA" function is turned ON, the tube current value to be applied to the X-ray tube is automatically calculated for each set scan position. Since a calculation result is shown in a format in which a scan position and a tube current value corresponding to the scan position are described as a list, the calculation result can be confirmed by the list.

However, if the calculation result is only shown by numerical values as the list, there is a problem in that it is difficult to grasp the relation between a set scan position and a tube current value. In particular, a recent "Auto mA" function has a plurality of modes such as a mode requiring high image quality, a mode requiring a smallest exposure amount, and an operator can select these modes. In this case, if the calculation result is only shown by numerical values as the list, a problem arises in that it is difficult to confirm, if the operator changes a mode, how the calculation result is changed.

Further, the tube current values calculated by "Auto mA" may include values which are not necessarily appropriate if they are individually examined. Conventionally, in these cases, there is no unit capable of individually correcting the calculated tube current values to arbitrary values.

To cope with the above problem, a positioning image obtained by a scout scan is shown as an X-ray CT function, and the image of a graph showing the correspondence relation to the tube current values as a control value of the amount of the X-ray of the X-ray tube at respective scan positions calculated by the "Auto mA" function is shown simultaneously with the positioning image being shown in a scan plan screen for setting the scan position of a subject to be diagnosed. Further, there is a technology for making it possible to change the tube current value at an arbitrary point on an image of a graph by dragging the point using a mouse (refer to, for example, Japanese Patent Application Publication No. 2002-177261).

However, the conventional technology assumes only to display a positioning image of a single imaging surface as a superimposed display. The conventional technology is not disadvantageous if the same current value is output while a CT scan is performed in one rotation. However, if a CT scan is performed in one rotation while changing the current value, the conventional technology can not show the change of the current value.

Further, an operator designates a standard deviation as an input value for determining "Auto mA". However, since the conventional technology displays only the image of the graph of a tube current value, if the tube current is changed, it cannot be anticipated that to what amount the standard deviation value is set. Further, it is difficult to sensuously grasp the relative relation between the variation ratio of the tube current value and the variation ratio of the standard deviation (how much change of mA results in how much change of standard deviation).

SUMMARY OF THE INVENTION

The present invention has taken into consideration the above-described problems, and it is a purpose of the present invention to provide an X-ray CT apparatus and a control method of the X-ray CT apparatus of the present invention which is capable of providing a reconstructed image desired by an operator while reducing exposure of an object to an X-ray.

To solve the above-described problems, the present invention provides the X-ray CT apparatus comprising: an irradiate unit configured to irradiate an X-ray; a determination unit configured to determinate a tube current value modulation to extend to a body axis direction in a predetermined rotation angle of the irradiate unit based on an index value to show a dispersion of CT values in required area in a reconstructed image, and a scan condition; and a displaying unit configured to align and display an image of the index value and an image of the tube current value modulation on an image used for positioning.

To solve the above-described problems, the present invention provides the control method of X-ray CT apparatus comprising: steps of: determinating a tube current value modulation to extend to a body axis direction in a predetermined rotation angle of a irradiate unit, which irradiate an X-ray, based on an index value to show a dispersion of CT values in required area in a reconstructed image, and a scan condition; and aligning and displaying an image of the index value and an image of the tube current value modulation on an image used for positioning.

BRIEF DESCRIPTION OF THE DRAWINGS

In the accompanying drawings:

FIGS. 6A and 6B are a schematic view showing an example of both displayed surfaces displayed on a display device;

DESCRIPTION OF THE PREFERRED EMBODIMENTS

Embodiments of an X-ray CT (computerized tomography) apparatus and a control method of the X-ray CT apparatus according to the present invention will be explained referring to the accompanying drawings.

Note that the X-ray CT apparatus has various types such as a ROTATE/ROTATE type, in which an X-ray tube device and an X-ray detector rotate around an object to be diagnosed together, a STATIONARY/ROTATE type, in which a lot of detection elements are arrayed in a ring-state and only an X-ray tube device rotates around the object to be diagnosed, and the like, and the present invention can be applied to any of the types.

First Embodiment

Figure 1:
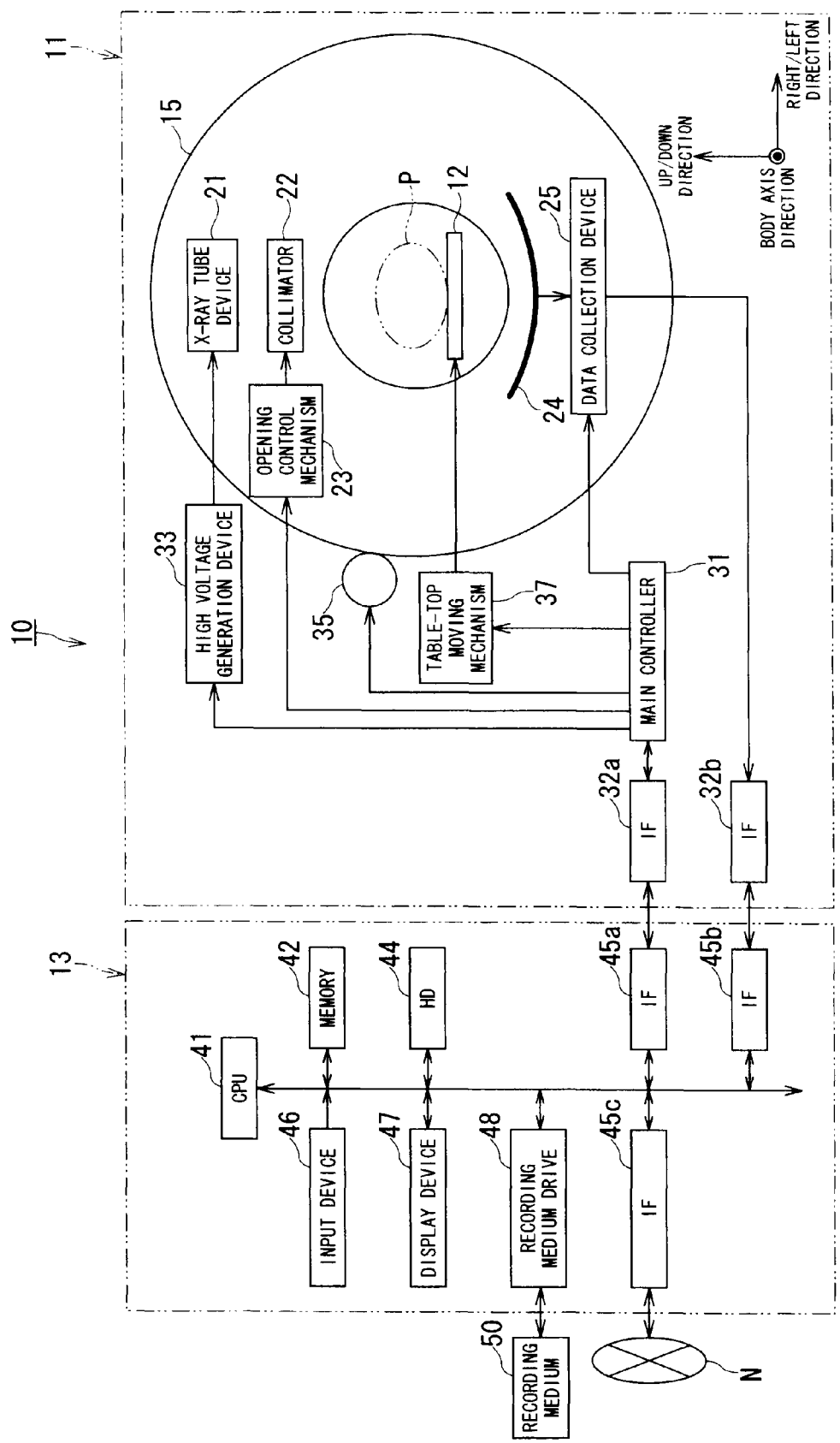
FIG. 1 is a schematic view showing a hardware structure of a first embodiment of an X-ray CT apparatus according to the present invention.

FIG. 1 is a schematic view showing a hardware structure of a first embodiment of an X-ray CT apparatus according to the present invention.

FIG. 1 shows the X-ray CT apparatus 10 of the first embodiment. If the X-ray CT apparatus 10 moves from an imaging region (portion) to a next imaging region in a series of a helical scan, it causes a scan center to approach to the body thickness center of an object (patient) P by moving a table-top 12 in a right/left direction, an up/down direction, or a combined direction of the right/left direction and the up/down direction. The X-ray CT apparatus 10 will be explained below as to an example in which the scan center is caused to approach to the body thickness center of the patient P in the up/down direction by moving the table-top 12 in the up/down direction if the imaging region in a series of the helical scan is moved to the next imaging region.

The X-ray CT apparatus 10 is an apparatus for reconstructing an image of an inside of the patient P by irradiating an X-ray to the patient P while changing a portion of the patient P to which the X-ray is irradiated and projecting the inside of the patient P inversely based on the X-ray transmitted through the patient P. The X-ray CT apparatus 10 finally generates sliced images and three-dimensional images of the inside of the patient P by performing a scan operation including respective operation stages for performing a scan (scanogram scan) for generating a positioning image, a helical scan, and a scan plan.

The X-ray CT apparatus 10 has a gantry unit 11 for scanning the patient P with an X-ray, a table-top 12, on which the patient P is placed and which is moved in a hollow portion of the gantry unit 11 in the right/left direction, the up/down direction, and a body axis direction of the patient P, and an operation console 13 for controlling the operation of the gantry unit 11 as well as reconstructing sliced images (axial images) and the like based on the data sent from the gantry unit 11 and outputting (displaying) them.

The gantry unit 11 can be operated in a tilt direction (not shown) and holds a rotating portion 15 and a fixed portion. Further, the rotating portion 15 of the gantry unit 11 holds an X-ray tube device 21, a collimator 22, an opening control mechanism 23, an X-ray detector 24, and a data collection device 25. The X-ray tube device 21 and the collimator 22, and the X-ray detector 24 are disposed at positions which confront with each other across the hollow portion of the gantry unit 11, i.e., across the patient P. The rotating portion 15 is arranged to rotate around the hollow portion in a state that it keeps the positional relation thereof.

The X-ray tube device 21 irradiates an X-ray from an X-ray tube (not shown) of the X-ray tube device 21 to the X-ray detector 24 by the power supplied from a high voltage generation device 33.

The collimator 22 has an opening for restricting the irradiation range of the X-ray irradiated from the X-ray tube device 21.

Further, a wedge filter (not shown), which is designed to have a thin central portion and thick edge portions, is interposed between the X-ray tube device 21 and the patient P. The wedge filter is used for a purpose of reducing a low energy component which is absorbed by the patient P and cannot reach the X-ray detector 24 and a purpose of matching the center of the dynamic range of the X-ray detector 24 to the periphery thereof.

The opening control mechanism 23 adjusts the opening width of the collimator 22 in response to a control signal from a main controller 31.

The X-ray detector 24 has detection elements (which may be detection elements having a plurality of different arrangements (the number of columns, the number of channels, and the like)) disposed in many columns to extend to the body axis direction to detect the X-ray supplied from the X-ray tube device 21 passing through the collimator 22 and the hollow portion. The detection elements are disposed side by side in at least 64 columns, for example, 256 columns in a slice direction of the X-ray detector 24.

The data collection device 25 is generally called a DAS (data acquisition system), amplifies a signal output from the X-ray detector 13 to each channel and further converts an analog signal to a digital signal. Converted data (raw data) is supplied to the external operation console 13 through an IF 32b of the gantry unit 11. Note that an interface (not shown) using a slip ring, an optical communication, and the like is interposed between the X-ray detector 24 and the data collection device 25. The interface permits the data collection device 25 to collect the output from the X-ray detector 24 while continuously rotating the gantry unit 11.

Further, the main controller 31, an IF (interface) 32a, the IF 32b, the high voltage generation device 33, a rotating/moving mechanism 35, and a table-top moving mechanism 37 are disposed to the fixed portion of the gantry unit 11.

The main controller 31 analyzes various commands received from the operation console 13 through the IF 32a and outputs various control signals to the high voltage generation device 33, the opening control mechanism 23, the rotating/moving mechanism 35, the table-top moving mechanism 37, and the data collection device 25 based on the commands.

The IFs 32a, 32b perform a communication control in accordance with respective standards.

The high voltage generation device 33 is a device for supplying power necessary to irradiate an X-ray to the X-ray tube device 21 and composed of a high voltage transformer, a filament heat converter, a rectifier, a high voltage switch device, and the like.

The rotating/moving mechanism 35 continuously rotates the rotating portion 15 in response to a drive signal from the main controller 31 so that the rotating portion 15 rotates around the hollow portion in a state that it keeps its positional relation.

The table-top moving mechanism 37 moves the table-top 12 in the right/left direction, the up/down direction, and the body axis direction of the patient P in response to a drive signal from the main controller 31.

The operation console 13 is basically composed of a computer and can perform a mutual communication with a network N of hospital LAN (local area network) and the like. The operation console 13 is roughly composed of basic hardware such as a CPU (central processing unit) 41 as a processor, a memory 42, a HD (hard disc) 44, IFs 45a, 45b, 45c, an input device 46, a display device 47, and the like. The CPU 41 is mutually connected to the respective hardware components which constitute the operation console 13 through a bus as a common signal transmission path. Note that the operation console 13 may have a recording medium drive 48.

If a command is input by that the input device 46 is operated by the operator, the CPU 41 executes a program stored to the memory 42. Otherwise, the CPU 41 loads a program stored to the HD 44, a program, which is transferred from the network N, received by the IF 45c, and installed on the HD 44, or a program, which is read out from a recording medium 50 mounted on the recording medium drive 48 and installed on the HD 44, on the memory 42 and executes it.

The memory 42 is a storage device which also acts as elements such as a ROM (read only memory), a RAM (random access memory), and the like and is used to store IPL (initial program loading), BIOS (basic input/output system), and data and temporarily store a work memory and data of the CPU 41.

The HD 44 is composed of a metal disk on which a magnetic substance is coated or vapor deposited and incorporated in a read-out device (not shown) so that it cannot be dismounted therefrom. The HD 44 is a storage device for storing a program (also including OS (operating system) and the like) in addition to an application program for setting a scan plan to be described later) installed on the operation console 13 and data such as the raw data, projection data, and data of a positioning image (an image used for positioning), a reconstructed image, and the like. Further, it is also possible to cause OS to provide GUI (graphical user interface) which permits the operator to frequently use graphics in order to show various kinds of information and to perform a basic operation by the input device 46.

The IFs 45a, 45b, 45c perform a communication control in accordance with respective standards. The IFs 45a, 45b perform communication with the gantry unit 11 and are connect to the IFs 32a, 32b of the gantry unit 11, respectively. Further, the IF 45c has a function capable of being connected to the network N through a phone line and the like, thereby the operation console 13 can be connected to the network N from the IF 45c.

A keyboard, a mouse, and the like, which can be operated by the operator, are exemplified as the input device 46, and an input signal is sent to the CPU 41 in accordance with an operation.

The display device 47 is composed of a D/A (digital/analog) converter, a monitor, and the like. A sliced image, a three-dimensional image, and the like are displayed on the display device 47 by developing image data and the like to a memory such as VRAM (video random access memory, not shown) and the like for developing image data which is intended to be displayed.

A recording medium can be mounted on and dismounted from the recording medium drive 48, and data (including a program) stored to the recording medium is read out and output to a bus, and further data supplied through the bus is written to the recording medium. The recording medium can be provided as so-called package software.

Figure 2:
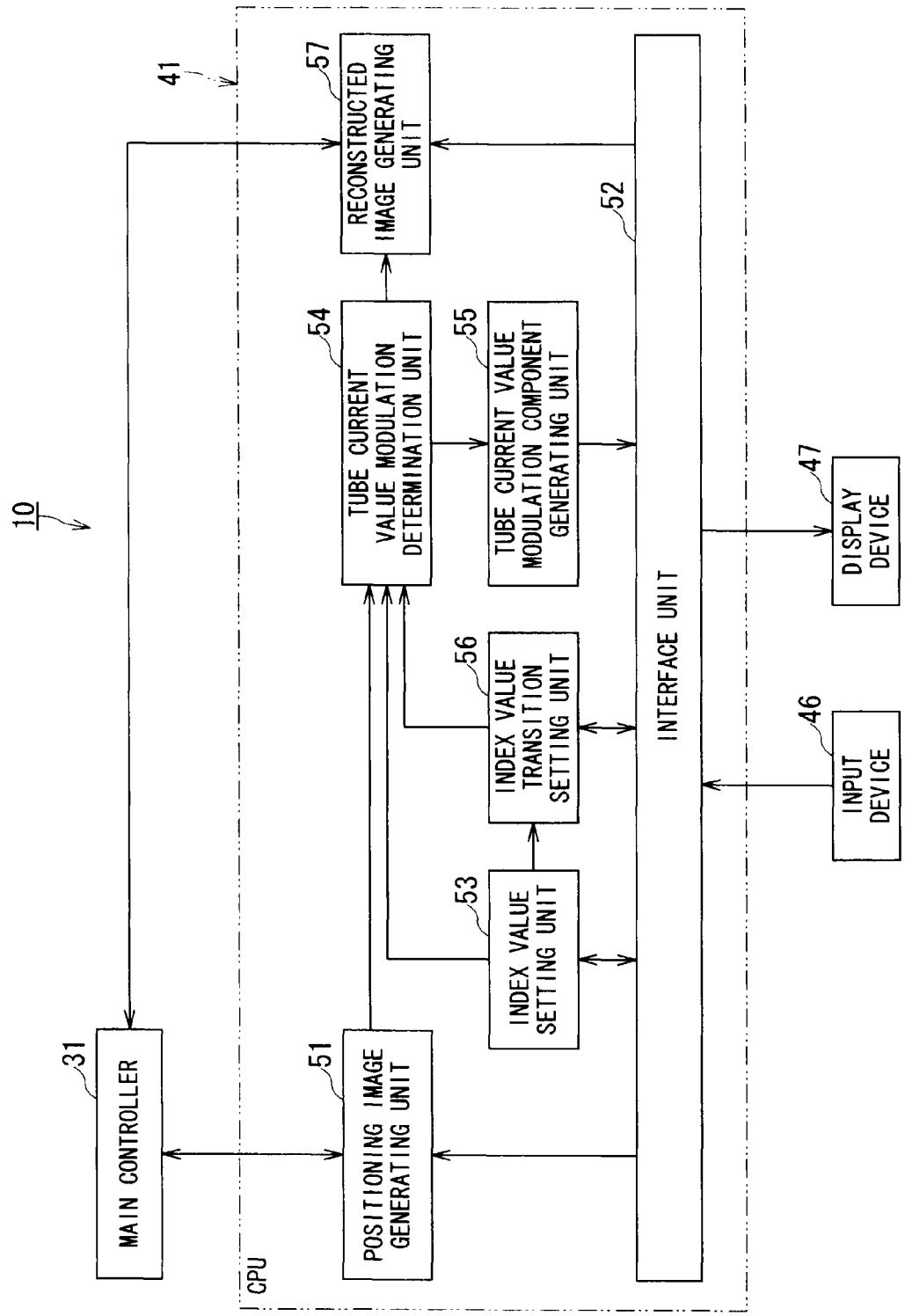
FIG. 2 is a block diagram showing a function of the X-ray CT apparatus of a first embodiment.

FIG. 2 is a block diagram showing a function of the X-ray CT apparatus 10 of the first embodiment.

If the CPU 41 shown in FIG. 1 executes a program, the X-ray CT apparatus 10 functions as a positioning image generating unit 51, an interface unit 52, an index value setting unit 53, a tube current value modulation determination unit 54, a tube current value modulation component generating unit 55, an index value transition setting unit 56, and a reconstructed image generating unit 57. Note that although it is assumed that the respective components 51 to 57 of the X-ray CT apparatus 10 are functioned by executing the program by the CPU 41, the present invention is not limited thereto. The components 51 to 57 of the X-ray CT apparatus 10 may be disposed to the X-ray CT apparatus 10 as hardware.

The positioning image generating unit 51 has a function for performing a scan for obtaining the positioning image by controlling the main controller 31 according to an input signal input, through interface unit 52, by input device 46 which an operator uses, and a function for generating a positioning image based on projection data obtained by the scan for obtaining the positioning image. If the scan for obtaining the positioning image is performed, the positioning image generating unit 51 controls the opening control mechanism 23, the high voltage generation device 33, the rotating/moving mechanism 35, and the table-top moving mechanism 37 through the main controller 31 based on scan conditions automatically selected by patient information such as a patient ID (identification), a patient name and the like. Or, if the scan for obtaining the positioning image is performed, the positioning image generating unit 51 controls the opening control mechanism 23, the high voltage generation device 33, the rotating/moving mechanism 35, and the table-top moving mechanism 37 through the main controller 31 based on scan conditions input from the input device 46 in a manual mode.

More specifically, if the scan for obtaining the positioning image is performed, the positioning image generating unit 51 performs imaging for obtaining the positioning image by irradiating an X-ray cone beam or an X-ray fan beam from one direction while moving the table-top 12 to extend to the body axis direction (while moving the gantry unit 11 to extend to the body axis direction) in a state that the rotation of the rotating portion 15 for holding the X-ray tube device 21 and the X-ray detector 24 is stopped. Note that the scan conditions means at least one of a body thickness of the patient P, a scan mode, exposure reduction ON/OFF, a slice thickness of imaging, a slice thickness of image, FOV (field of view), a helical pitch, a reconstruction function, a tube voltage, a tube current, and a scan speed.

Note that the positioning image generating unit 51 may generate positioning images of a plurality of imaging surfaces, for example, two imaging surfaces. A case, in which the positioning image generating unit 51 generates positioning images of two imaging surfaces (an upper surface and a side surface of the patient P), will be explained as example. However, the present invention is not limited to the case in which the positioning images of the two imaging surfaces are generated.

The interface unit 52 is interface such as the GUI. The GUI uses many graphic for displaying to the display device 47 for the operator, and can perform a fundamental operation by the input device 46.

The index value setting unit 53 has a function for setting an index value, obtained each one round of the X-ray tube device 21, to show a dispersion of CT values in required area in a reconstructed image, for example, an image SD (standard deviation) value, according to an input signal input though the interface unit 52 by the input device 46. Because the body thicknesses are different each imaging region, it is suitable that the index value setting unit 53 sets a different index value each imaging region, respectively.

The tube current value modulation determination unit 54 has a function for determining a tube current value modulation (Volume EC) according to the rotation angle (also called an X-ray irradiation angle and a cone angle) of the X-ray tube device 21 for irradiating an X-ray and to the position of the patient P to extend to the body axis direction based on the scan conditions set or selected by the positioning image generating unit 51, and the index value set by the index value setting unit 53. The tube current value modulation is determined by a technology called a "modulation" which changes X-ray conditions depending on the thickness of the patient P as to the rotation angle of the X-ray tube device 21 assuming the thickness (cross section in the right/left direction–the up/down direction) of the patient P as, for example, an oval shape.

The tube current value modulation component generating unit 55 has a function for generating a tube current value modulation component, obtained each imaging surface, to extend to the body axis direction in a predetermined rotation angle of the X-ray tube device 21 among the tube current value modulation determined by the tube current value modulation determination unit 54. If, for example, the imaging surface of the positioning image is a side surface (cross section in up/down direction–body axis direction) of the patient P, the tube current value modulation component generating unit 55 generates the tube current value modulation component to extend to the body axis direction in 90 degrees of the rotation angle of the X-ray tube device 21 among the tube current value modulation. Further, if, for example, the imaging surface of the positioning image is an upper surface (cross section in right/left direction–body axis direction) of the patient P, the tube current value modulation component generating unit 55 generates the tube current value modulation component to extend to the body axis direction in 0 degree of the rotation angle of the X-ray tube device 21 among the tube current value modulation.

Figure 3:
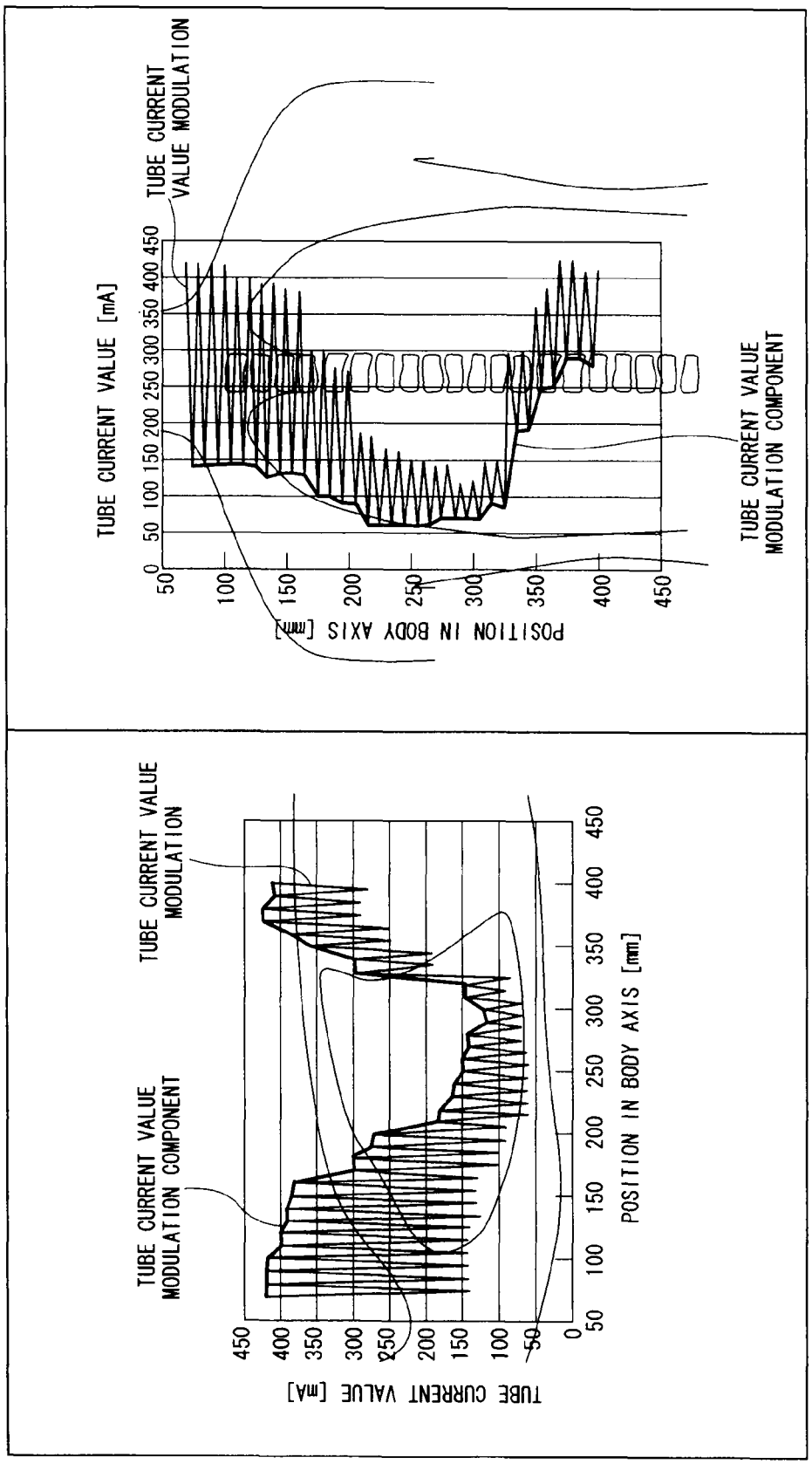
FIG. 3 is a schematic view explaining a generating method of a tube current value modulation component to extend to a body axis direction.

FIG. 3 is a schematic view explaining a generating method of the tube current value modulation component to extend to the body axis direction.

A left side of FIG. 3 shows a positioning image whose the imaging surface is the side surface (cross section in up/down direction–body axis direction) of the patient P an image of a graph (vertical axis: tube current value [mA], horizontal axis: position [mm] in body axis direction) of tube current value modulation determined by the tube current value modulation determination unit 54. The position to extend to the body axis direction of the positioning image corresponds to the position to extend to the body axis direction of the graph of the tube current value modulation. As shown on the left side of FIG. 3, the tube current value modulation component to extend to the body axis direction in 90 degrees of the rotation angle of the X-ray tube device 21 is shown in the tube current value modulation as a line for connecting maximum peak values of the tube current value modulation included in a graph overlapped on the positioning image whose the imaging surface is the side surface of the patient P.

In contrast, a right side of FIG. 3 shows a positioning image whose the imaging surface is an upper surface (cross section in right/left direction–body axis direction) of the patient P, and an image of a graph (vertical axis: position [mm] in body axis direction, horizontal axis: tube current value [mA]) of tube current value modulation determined by the tube current value modulation determination unit 54. The position to extend to the body axis direction of the positioning image corresponds to the position to extend to the body axis direction of the graph of the tube current value modulation. As shown on the right side of FIG. 3, the tube current value modulation component to extend to the body axis direction in 0 degree of the rotation angle of the X-ray tube device 21 is shown in the tube current value modulation as a line for connecting minimum peak values of the tube current value modulation included in a graph overlapped on the positioning image whose the imaging surface is the upper surface of the patient P.

Further, the interface unit 52 shown in FIG. 2 generates the positioning images of two imaging surfaces and an image of a graph showing the tube current value modulation component to extend to the body axis direction of respective imaging surfaces generated by the tube current value modulation component generating unit 55 for the respective imaging surfaces and displaying them on the display device 47 at the same time. Further, the interface unit 52 generates the positioning images of two imaging surfaces and an image of a graph showing the tube current value modulation component to extend to the body axis direction of respective imaging surfaces determined by the tube current value modulation determination unit 54 for the respective imaging surfaces and displaying them on the display device 47 at the same time.

Figure 4:
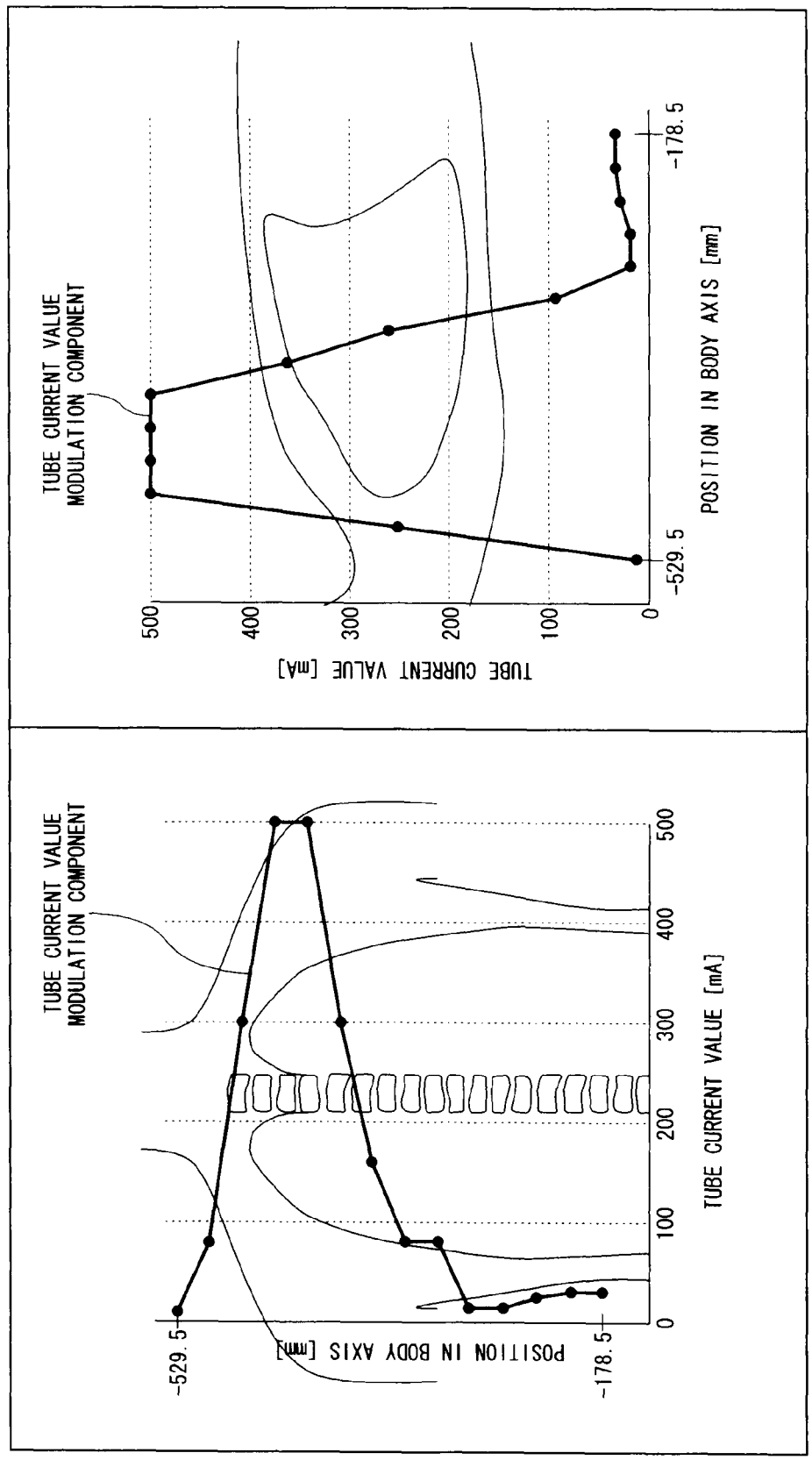
FIG. 4 is a schematic view showing an example of two-image information shown in an image of a graph showing a positioning image and a tube current value modulation component to extend to the body axis direction.

FIG. 4 is a schematic view showing an example of two-image information shown in an image of a graph showing a positioning image and the tube current value modulation component to extend to the body axis direction.

A left side of FIG. 4 shows two-image information shown by the positioning image whose imaging surface is the upper surface of the patient P (cross section in right/left direction–body axis direction) and an image of a graph of the tube current value modulation component (shown in the graph on the right side of FIG. 3) to extend to the body axis direction in 0 degree of the rotation angle of the X-ray tube device 21 generated by the tube current value modulation component generating unit 55. In contrast, a right side of FIG. 4 shows two-image information shown by a positioning image whose the imaging surface is the side surface of the patient P (cross section in up/down direction–body axis direction) and an image of a graph of a tube current value modulation component (shown in the graph on the left side of FIG. 3) to extend to the body axis direction in 90 degrees of the rotation angle of the X-ray tube device 21 generated by the tube current value modulation component generating unit 55. Note that the position to extend to the body axis direction of the positioning image corresponds to the position to extend to the body axis direction of the graph of the tube current value modulation.

Further, the index value transition setting unit 56 shown in FIG. 2 has a function for setting an index value transition, obtained each imaging surface, that the index value set by the index value setting unit 53 is set to extend to the body axis direction. If the index value transition setting unit 56 is provided, the interface unit 52 generates two positional image in two imaging surface, an image of a graph showing the tube current value modulation component to extend to the body axis direction of each imaging surface generated by the tube current value modulation component generating unit, and an image of a graph showing the index value transition to extend to the body axis direction of each imaging surface set by the index value transition setting unit 56 to each imaging surface and has a function for showing them on the display device 47 at the same time.

Figure 5:
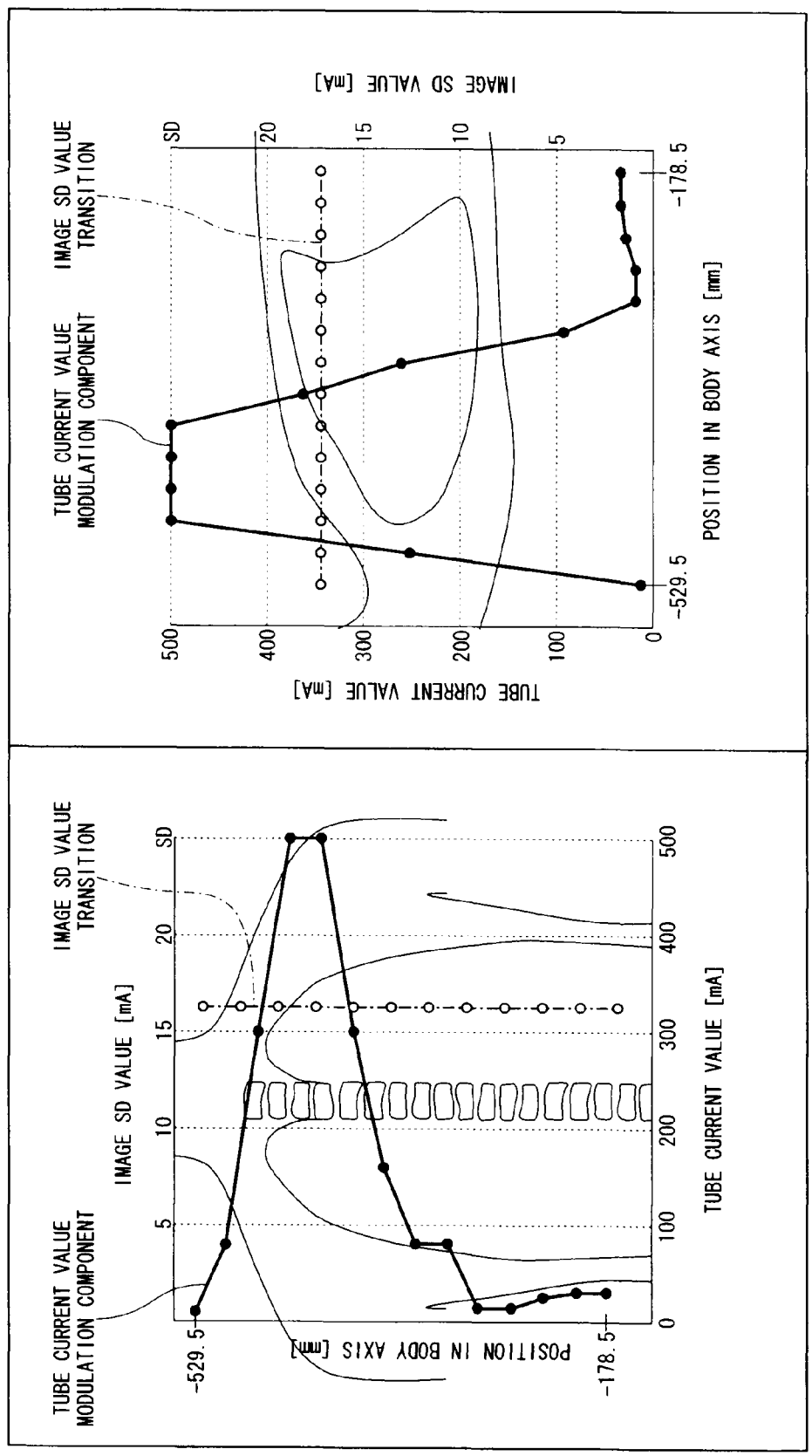
FIG. 5 is a schematic view showing an example of three-image information shown by the positioning image, an image of a graph showing the tube current value modulation component to extend to the body axis direction, and an image of a graph showing an index value transition to extend to the body axis direction.

FIG. 5 is a schematic view showing an example of three-image information shown by the positioning image, an image of a graph showing the tube current value modulation component to extend to the body axis direction, and an image of a graph showing the index value transition to extend to the body axis direction.

A left side of FIG. 5 shows three-image information shown by a positioning image whose the imaging surface is the upper surface of the patient P (cross section in right/left direction–body axis direction), an image of a graph of a tube current value modulation component (shown in the graph on the right side of FIG. 3) to extend to the body axis direction in 0 degree of the rotation angle of the X-ray tube device 21 generated by the tube current value modulation component generating unit 55, and image of a graph (longitudinal axis: position [mm] to extend to the body axis direction, upper horizontal axis: image SD value [mA] as index value transition to extend to the body axis direction) showing the index value transition to extend to the body axis direction set by the index value transition setting unit 56. The position to extend to the body axis direction of the positioning image corresponds to the position to extend to the body axis direction of the graph of the tube current value modulation.

In contrast, a right side of FIG. 5 shows three-image information shown by a positioning image whose the imaging surface is the side surface of the patient P (cross section in up/down direction–body axis direction), an image of a graph of a tube current value modulation component (shown in the graph on the left side of FIG. 3) to extend to the body axis direction in 90 degrees of the rotation angle of the X-ray tube device 21 generated by the tube current value modulation component generating unit 55, and an image of a graph (right longitudinal axis: image SD value [mA] as index value transition to extend to the body axis direction, horizontal axis: position [mm] to extend to the body axis direction) showing the index value transition to extend to the body axis direction in 90 degrees of the rotation angle of the X-ray tube device 21 set by the index value transition setting unit 56. The position to extend to the body axis direction of the positioning image corresponds to the position to extend to the body axis direction of the graph of the tube current value modulation.

Figure 6A:
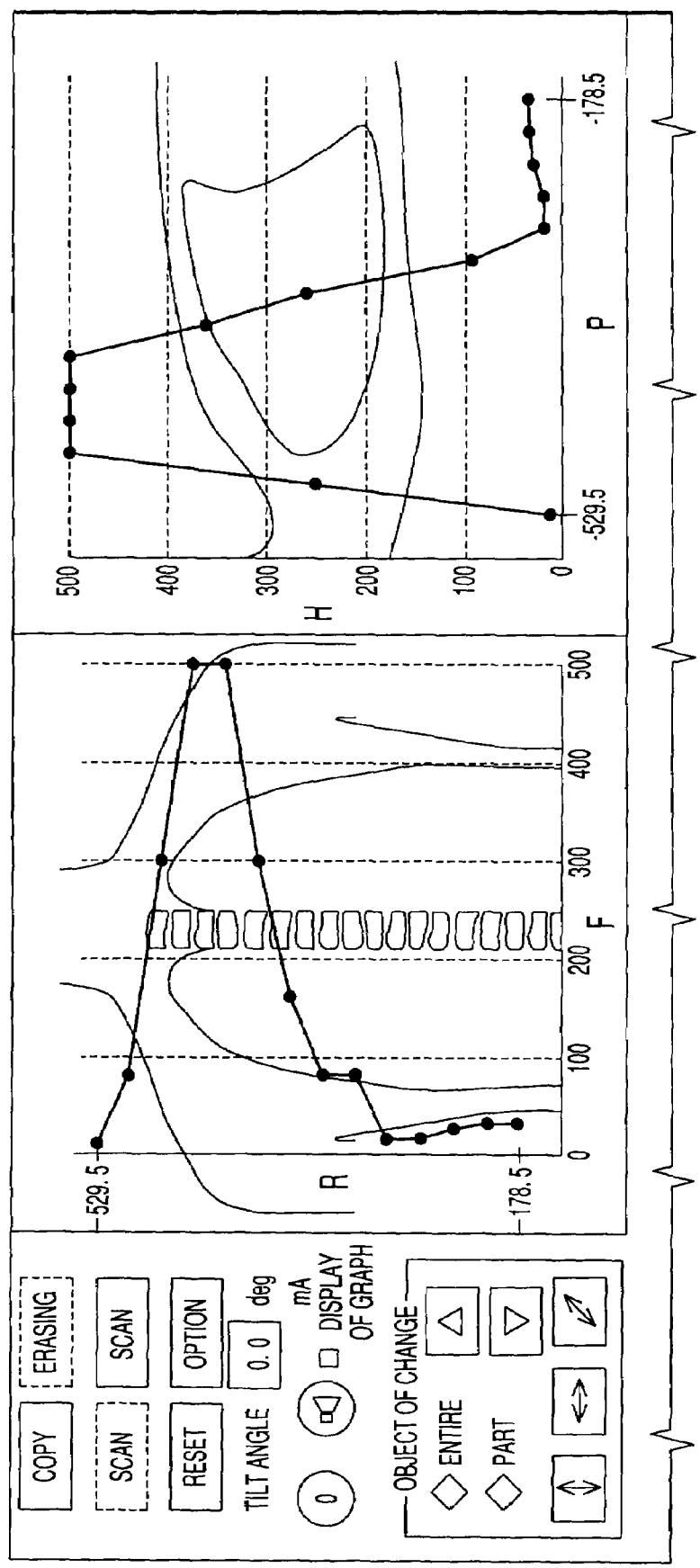
Figure 6B:
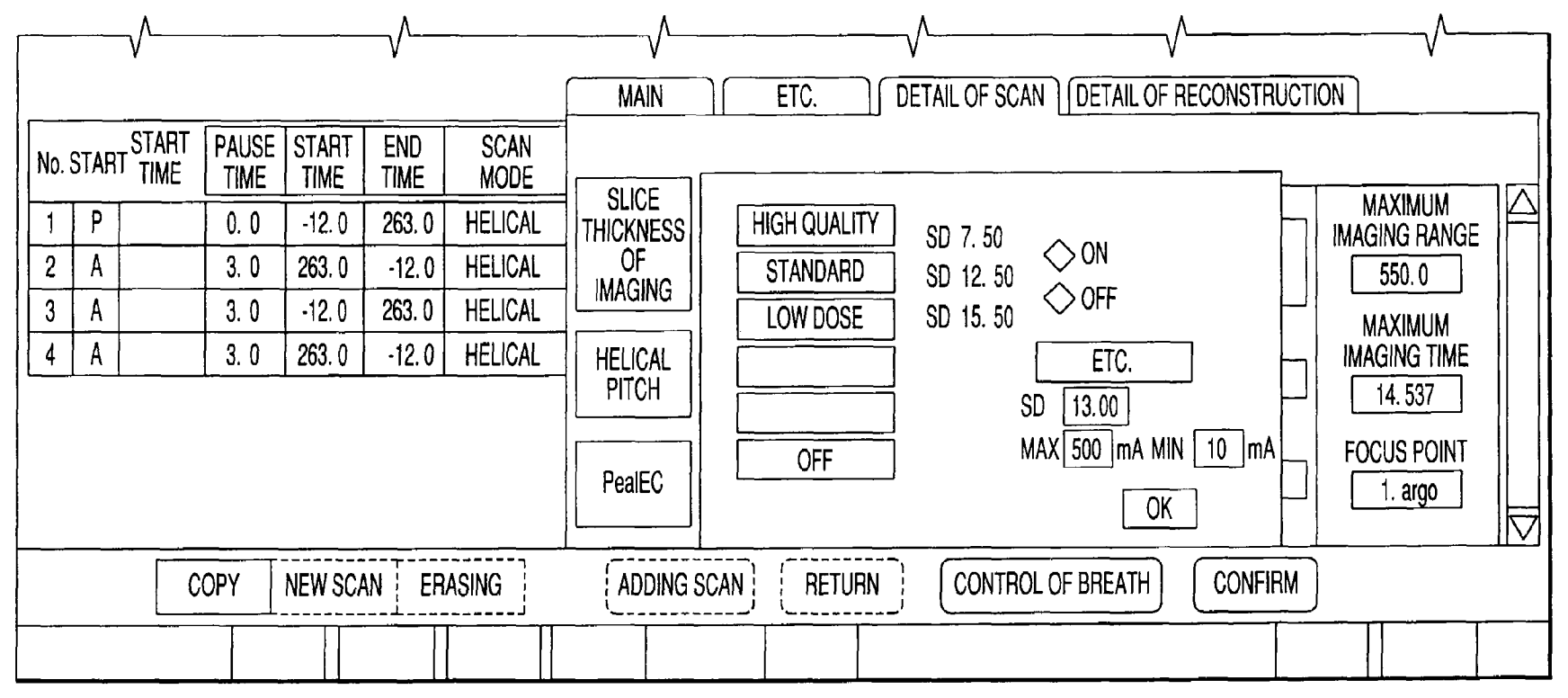

FIGS. 6A and 6B are is a schematic view showing an example of both displayed surfaces displayed on the display device 47. FIGS. 6A and 6B are shows both surfaces for displaying the two-image information of each imaging surface shown in FIG. 4 and various parameters.

Further, the index value transition setting unit 56 has a function shown in FIG. 2 for changing and setting the index value transition to extend to the body axis direction included in the graph displayed simultaneously with the positioning image of each imaging surface in response to an input signal from the interface unit 52 after the three-image information is displayed by the interface unit 52. The index value transition setting unit 56 sets the index value transition to extend to the body axis direction to each imaging surface after the entire index value transition is changed by interactively slidingly moving the entire index value transition to extend to the body axis direction included in the image of the graph displayed simultaneously with the imaging surface selected from two imaging surfaces, for example, the positioning image of the side surface. Further, the index value transition setting unit 56 sets the index value transition to extend to the body axis direction to all the imaging surfaces after it is partly changed by interactively moving a part (each one round of the X-ray tube device 21 as minimum unit that can be changed) of the index value transition to extend to the body axis direction included in the image of the graph displayed simultaneously with the selected positioning image of the side surface.

If the index value transition to extend to the body axis direction is changed and set by the index value transition setting unit 56, the tube current value modulation determination unit 54 determines the tube current value modulation based on the index value transition to extend to the body axis direction, which is set to each imaging surface by the index value transition setting unit 56, after it is entirely (partly) changed. The tube current value modulation component generating unit 55 generates the tube current value modulation component to extend to the body axis direction to each imaging surface based on the tube current value modulation determined by the tube current value modulation determination unit 54 based on the index value transition.

Here, the interface unit 52 has a function for controlling an input from the input device 46 for changing the index value transition to extend to the body axis direction by slidingly moving the entire index value transition to extend to the body axis direction or partly moving the index value transition to extend to the body axis direction (index value corresponding to a position to extend to the body axis direction) if the index value transition to extend to the body axis direction is changed and set by the index value transition setting unit 56. When the index value transition to extend to the body axis direction is entirely or partly changed, there can be employed an arrangement in which the interface unit 52 permits, for example, a mouse as the input device 46 to perform a drag/drop operation, an arrangement in which a keyboard as the input device 46 permits a slide bar displayed through a monitor of the display device 47 to be moved, and an arrangement in which a numerical value can be input by the keyboard as the input device 46. Further, If the index value transition to extend to the body axis direction is partly changed, the interface unit 52 is arranged such that it can perform the drag/drop operation by, for example, the mouse as the input device 46.

When an input is performed by the keyboard as the input device 46 to partly change the index value transition to extend to the body axis direction through the interface unit 52 based on the image of the graph showing the index value transition to extend to the body axis direction being displayed, a pointer, which is displayed in association with the movement of the mouse if the index value transition to extend to the body axis direction is partly changed, does not overlap on the positioning image. With this arrangement, if the operator desires to partly change the index value transition to extend to the body axis direction in a minute unit, the operator can observe a change of the graph showing the index value transition in the body direction and a change of the graph showing the tube current value modulation component to extend to the body axis direction which is caused by the change of the index value transition in the body direction while keeping a state in which the positioning image can be easily observed. Further, the operator can determine the amount of change and the like of the index value transition to extend to the body axis direction by preset.

Note that if it is possible to make an input to entirely (partly) change the index value transition to extend to the body axis direction by the mouse as the input device 46 through the interface unit 52 base on the image of the graph showing the index value transition to extend to the body axis direction being displayed, a change of the graph showing the index value transition in the body direction and a change of the graph showing the tube current value modulation component to extend to the body axis direction caused by the above change are continuously displayed through the monitor of the display device 47 even while a drag is being performed. With this operation, the operator can continuously observe the change of the index value transition to extend to the body axis direction and the change of the tube current value modulation component to extend to the body axis direction through the monitor.

Figure 7:
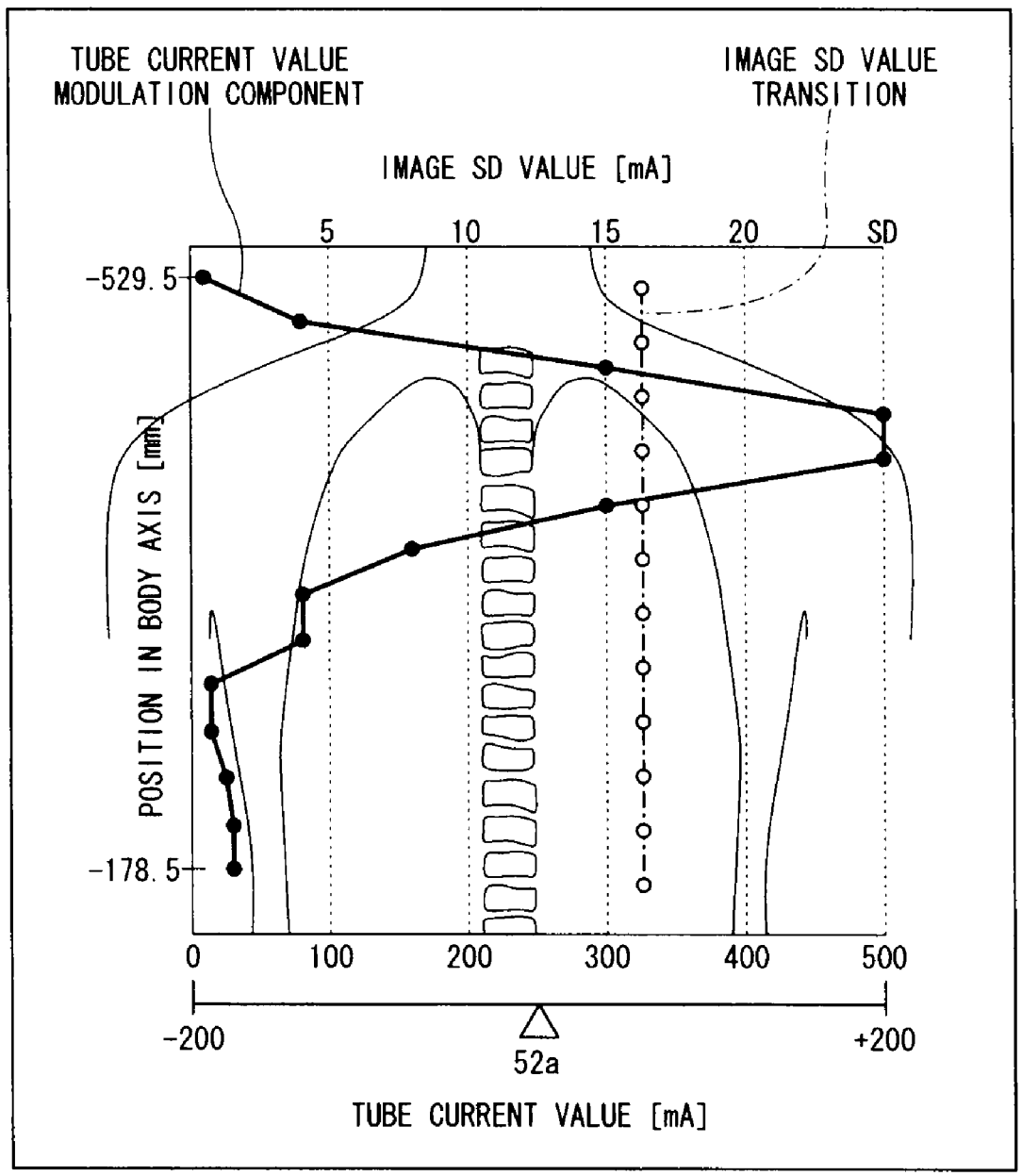
FIG. 7 is a schematic view explaining a function of a interface unit if the index value transition to extend to the body axis direction is changed.

FIG. 7 is a schematic view explaining the function of the interface unit 52 if the index value transition to extend to the body axis direction is changed.

FIG. 7 shows the interface unit 52 which permits an input to be performed to the image including the three-image information shown in the left side of FIG. 5 to change the entire index value transition to extend to the body axis direction by moving a slide bar 52a using the input device 46.

As shown in FIG. 7, if the image of the graph showing the tube current value modulation component to extend to the body axis direction, the image of the graph showing the index value transition to extend to the body axis direction, and the image including the three-image information by the positioning image are shown at the same time, the index value transition to extend to the body axis direction can be entirely changed while comparing the index value transition to extend to the body axis direction with the tube current value modulation component to extend to the body axis direction. Further, since the information that how much the tube current value modulation component to extend to the body axis direction is changed in the right/left direction if how much the index value transition to extend to the body axis direction is entirely changed in the right/left direction can be visually obtained, the operator can more sensuously find the relation between the tube current value modulation component to extend to the body axis direction and the index value transition to extend to the body axis direction. Accordingly, this assists the operator when he or she broadens the range of judgment of the scan plan.

Note that the interface unit 52 displays at least one of the image of the graph showing the tube current value modulation component to extend to the body axis direction and the image of the graph showing the index value transition to extend to the body axis direction as shown in FIG. 7 following to the pan information and the zoom information of the positioning image. It is possible to recognize and change an index value, which is a part of the index value transition to extend to the body axis direction, in a minute unit through the monitor by combining the pan information and the zoom information.

Further, the reconstructed image generating unit 57 shown in FIG. 2 has a function for performing a helical scan by controlling the main controller 31 according to an input signal input, through interface unit 52, by input device 46 which an operator uses while changing the amount of an X-ray according to the tube current value modulation determined by the tube current value modulation determination unit 54, and for generating a reconstructed image based on projection data in the direction of about 360 degrees, obtained by the helical scan. The reconstructed image generating unit 57 images a sliced image by controlling the main controller 31 according to the tube current value modulation determined by the tube current value modulation determination unit 54, continuously rotating the rotating portion 15 which holds the X-ray tube device 21 and the X-ray detector 24, and irradiating an X-ray cone beam or an X-ray fan beam from the angle of about 360 degrees (180 degrees+view angle) while moving the table-top 12 to extend to the body axis direction (while moving the gantry unit 11 to extend to the body axis direction).

Then, the reconstructed image generating unit 57 executes correction processes such as a logarithm conversion process, a sensitivity correction process, and the like to raw data which is input from the data collection device 25 of the gantry unit 11 through the IF 45b shown in FIG. 1 and projected in one direction. The raw data in the one direction subjected to the various corrections is stored once to a storage device such as the HD 44 and the like. Note that the raw data in the one direction is called "projection data". Note that the projection data may be subjected to a scattering line removal process. Further, the reconstructed image is generated using reconstructing methods such as a fan beam reconstructing which assumes that back-projection paths in the slice direction are parallel with each other, a cone beam reconstructing which takes the rotation angle of the X-ray tube device 21 in the slice direction into consideration, and the like based on the projection data.

The X-ray CT apparatus 10 of the first embodiment can provide a more correct tube current value determination function with the operator by displaying the images, which include the two-image information shown by the image of the graph showing the positioning image and the tube current value modulation component to extend to the body axis direction and the three-image information shown by the image of the graph showing the positioning image and the tube current value modulation component to extend to the body axis direction and the image of the graph showing the index value transition to extend to the body axis direction, to each image surface of the graph of the positioning image at the stage of the scan plan. Further, a burden on the patient P can be reduced by the reduction of exposure to the X-ray achieved by the above arrangement.

According to the X-ray CT apparatus 10 of the first embodiment, there can be provided the reconstructed image desired by the operator while reducing exposure of the patient P to the X-ray.

Second Embodiment

Since a hardware arrangement of an X-ray CT apparatus 10A of a second embodiment is the same as that of the X-ray CT apparatus 10 of the first embodiment shown in FIG. 1, the explanation thereof is omitted.

Figure 8:
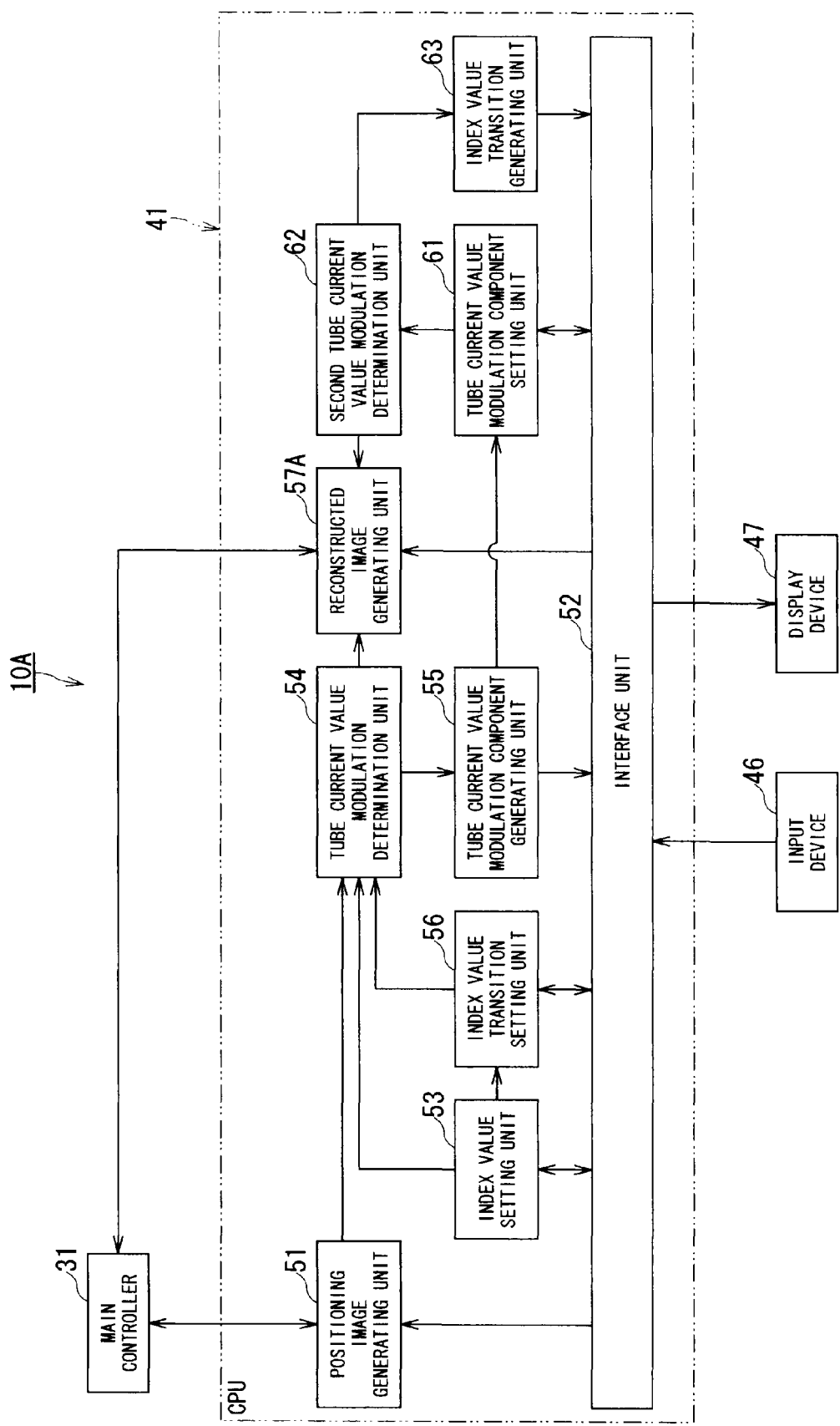
FIG. 8 is a block diagram showing a function of the X-ray CT apparatus 10A of a second embodiment.

FIG. 8 is a block diagram showing a function of the X-ray CT apparatus 10A of the second embodiment.

If the CPU 41 shown in FIG. 1 executes a program, the X-ray CT apparatus 10A functions as a positioning image generating unit 51, an interface unit 52A, an index value setting unit 53, a first tube current value modulation determination unit 54, a tube current value modulation component generating unit 55, an index value transition setting unit 56, a reconstructed image generating unit 57A, a tube current value modulation component setting unit 61, a second tube current value modulation determination unit 62, and an index value transition generating unit 63. Note that although it is assumed that the respective components 51 to 63 of the X-ray CT apparatus 10A are functioned by executing the program by the CPU 41, the present invention is not limited thereto. The components 51 to 63 of the X-ray CT apparatus 10A may be disposed to the X-ray CT apparatus 10A as hardware.

The first tube current value modulation determination unit 54 has the same function as that of the tube current value modulation determination unit 54 shown in FIG. 2.

The tube current value modulation component setting unit 61 has a function for changing and setting a tube current value modulation component in the body axis direction included in an image of a graph which is simultaneously displayed with a positioning image of each imaging surface in response to an input signal from the interface unit 52 after the two-image information or the three-image information is displayed by the interface unit 52 as explained in the first embodiment. The tube current value modulation component setting unit 61 sets a tube current value modulation component to extend to the body axis direction after it is entirely changed to each imaging surface by interactively slidingly the imaging surface that is selected from two imaging surfaces, for example, the entire tube current value modulation component to extend to the body axis direction that is included in an image of a graph displayed simultaneously with the positioning image of the side surface. Further, the tube current value modulation component setting unit 61 sets the tube current value modulation component to extend to the body axis direction to all the imaging surfaces after it is partly changed by interactively moving a part (minimum unit that can be changed) of the tube current value modulation component to extend to the body axis direction included in an image of a graph displayed simultaneously with the selected positioning image of the side surface.

If the tube current value modulation component setting unit 61 changes the tube current value modulation component to extend to the body axis direction after the image including the two-image information or the three-image information is displayed by the interface unit 52, the interface unit 52 has a function for controlling an input for changing the tube current value modulation component to extend to the body axis direction by entirely moving the tube current value modulation component to extend to the body axis direction from the input device 46 or moving a part (tube current value corresponding to a certain position to extend to the body axis direction) of the component. When the tube current value modulation component to extend to the body axis direction is entirely or partly changed, there can be employed an arrangement in which the interface unit 52 permits, for example, a mouse as the input device 46 to perform a drag/drop operation, an arrangement in which a keyboard as the input device 46 permits a slide bar displayed through a monitor of the display device 47 to be moved, and an arrangement in which a numerical value can be input by the keyboard as the input device 46. Further, if the tube current value modulation component to extend to the body axis direction is partly changed, the interface unit 52 is arranged such that it can perform the drag/drop operation by, for example, the mouse as the input device 46.

The second tube current value modulation determination unit 62 has a function for generating a tube current value modulation after it is entirely (partly) changed based on the tube current value modulation component to extend to the body axis direction which is set by the tube current value modulation component setting unit 61 after it is entirely (partly) changed to each imaging surface.

The index value transition generating unit 63 has a function for generating an index value transition to extend to the body axis direction after it is entirely (partly) changed based on the tube current value modulation which is set by the second tube current value modulation determination unit 62 after it is entirely (partly) changed.

The interface unit 52 has a function for generating and simultaneously showing three-image information, which includes an image of a graph showing the tube current value modulation component to extend to the body axis direction set by the tube current value modulation component setting unit 61 after it is entirely (partly) changed to each image surface, an image of a graph showing the index value transition to extend to the body axis direction generated by the index value transition generating unit 63 after it is entirely (partly) changed, and a positioning image, in addition to function of the interface unit 52 shown in FIG. 2.

The reconstructed image generating unit 57A has a function for performing a helical scan by controlling the main controller 31 according to an input signal input, through interface unit 52, by input device 46 which an operator uses while changing the amount of an X-ray according to the tube current value modulation determined by the second tube current value modulation determination unit 62 in addition to the function of the reconstructed image generating unit 57 shown in FIG. 2, and for generating a reconstructed image based on projection data in the direction of about 360 degrees, obtained by the helical scan. The reconstructed image generating unit 57A images a sliced image by controlling a main controller 31 according to the tube current value modulation determined by the second tube current value modulation determination unit 62, continuously rotating a rotating portion 15 which holds the X-ray tube device 21 and an X-ray detector 24, and irradiating an X-ray cone beam or an X-ray fan beam from the angle of about 360 degrees (180 degrees+view angle) while moving a table-top 12 to extend to the body axis direction (while moving a gantry unit 11 to extend to the body axis direction).

Then, the reconstructed image generating unit 57 executes correction processes such as a logarithm conversion process, a sensitivity correction process, and the like to raw data which is input from a data collection device 25 of the gantry unit 11 through the IF 45b shown in FIG. 1 and projected in one direction, is subjected to. The raw data in the one direction subjected to the various corrections is stored once to a storage device such as the HD 44 and the like. Further, the reconstructed image is generated using reconstructing methods such as a fan beam reconstructing which assumes that back-projection paths in the slice direction are parallel with each other, a cone beam reconstructing which takes the rotation angle of the X-ray tube device 21 in the slice direction into consideration, and the like based on the projection data.

Note that the components of the X-ray CT apparatus 10A, which are shown in FIG. 8 and the same as those of the X-ray CT apparatus 10 shown in FIG. 2, are denoted by the same reference numerals, and the explanation thereof is omitted. When an input is performed by the keyboard as the input device 46 to partly change the tube current value modulation component to extend to the body axis direction through the interface unit 52 based on the image of the graph showing the tube current value modulation component to extend to the body axis direction which is displayed by the tube current value modulation component setting unit 61 simultaneously with the positioning image of each imaging surface after two-image information or three-image information is displayed by the interface unit 52, a pointer, which is displayed in association with the movement of the mouse if the tube current value modulation component to extend to the body axis direction is partly changed, does not overlap on the positioning image. With this arrangement, if the operator desires to partly change the tube current value modulation component to extend to the body axis direction in a minute unit, the operator can observe a change of the graph showing the index value transition in the body direction and a change of the graph showing the index value transition to extend to the body axis direction which is caused by the change of the tube current value modulation component in the body direction while keeping a state in which the positioning image can be easily observed. Further, the operator can determine the amount of change and the like of the tube current value modulation component to extend to the body axis direction by preset.

Note that if it is possible to make an input to entirely (partly) change the tube current value modulation component to extend to the body axis direction by the mouse as the input device 46 through the interface unit 52 base on the image of the graph showing the tube current value modulation component to extend to the body axis direction being displayed, a change of the graph showing the tube current value modulation component in the body direction and a change of the graph showing the index value transition to extend to the body axis direction caused by the above change are continuously displayed through a monitor of the display device 47 even while a drag is being performed. With this operation, the operator can continuously observe the change of the tube current value modulation component to extend to the body axis direction and the change of the index value transition to extend to the body axis direction through the monitor.

The X-ray CT apparatus 10A of the second embodiment can provide a more correct tube current value determination function with the operator by displaying the images, which include the two-image information shown by the image of the graph showing the positioning image and the tube current value modulation component to extend to the body axis direction and the three-image information shown by the image of the graph showing the positioning image and the tube current value modulation component to extend to the body axis direction and the image of the graph showing the index value transition to extend to the body axis direction, to each imaging surface of the graph of the positioning image at the stage of a scan plan. Further, a burden on a patient P can be reduced by the reduction of exposure to an X-ray achieved by the above arrangement.

According to the X-ray CT apparatus 10A of the second embodiment, there can be provided the reconstructed image desired by the operator while reducing exposure of the patient P to the X-ray.

What is claimed is:

1. An X-ray CT apparatus comprising:
   an irradiation unit configured to emit an X-ray;
   a determination unit configured to determine a tube current value modulation to extend along a body axis direction in a predetermined rotation angle of the irradiation unit based on an index value to show a dispersion of CT values in a required area in a reconstructed image, and a scan condition; and
   a displaying unit configured to (1) display a value image of the index value or the tube current value modulation by superimposing the value image on an image used for positioning and (2) align the superimposed image so that a positional axis of the superimposed image extends along the body axis direction.

2. The X-ray CT apparatus according to claim 1, wherein the determination unit is configured to assume the index value as a standard deviation value to show the dispersion.

3. The X-ray CT apparatus according to claim 1, further comprising a unit configured to perform a helical scan while changing the amount of an X-ray according to the tube current value modulation.

4. The X-ray CT apparatus according to claim 1, further comprising a unit configured to be capable of changing an entire of an index value transition, in which the index value is set to extend to the body axis direction, wherein
   the determination unit is configured to determine the tube current value modulation based on the changed index value transition.

5. The X-ray CT apparatus according to claim 1, further comprising a unit configured to be capable of changing part of an index value transition, in which the index value is set to extend to the body axis direction, wherein
   the determination unit is configured to determine the tube current value modulation based on the changed index value transition.

6. The X-ray CT apparatus according to claim 1, further comprising:
   a unit configured to generate a tube current value modulation component to extend to the body axis direction in a predetermined rotation angle of the irradiation unit among the tube current value modulation;
   a unit configured to be capable of changing the entire tube current value modulation component;
   a second determination unit configured to determine a changed tube current value modulation based on the changed tube current value modulation component; and
   a unit configured to generate an index value transition based on the changed tube current value modulation, wherein
   the displaying unit is configured to align and display an image of the index value transition and the changed tube current value modulation on the image used for positioning.

7. The X-ray CT apparatus according to claim 1, further comprising:
   a unit configured to generate a tube current value modulation component to extend to the body axis direction in a predetermined rotation angle of the irradiation unit among the tube current value modulation;
   a unit configured to be capable of changing part of the tube current value modulation component;
   a second determination unit configured to determine a changed tube current value modulation based on the changed tube current value modulation component; and
   a unit configured to generate an index value transition based on the changed tube current value modulation, wherein
   the displaying unit is configured to align and display an image of the index value transition and the changed tube current value modulation on the image used for positioning.

8. The X-ray CT apparatus according to claim 1, wherein the determination unit is configured to set a different index value each imaging region, respectively.

9. A control method for an X-ray CT apparatus comprising steps of:

determining a tube current value modulation to extend along a body axis direction in a predetermined rotation angle of an irradiation unit, which emits an X-ray, based on an index value to show a dispersion of CT values in a required area in a reconstructed image, and a scan condition; and displaying a value image of the index value or the tube current value modulation by superimposing the value image on an image used for positioning and aligning the superimposed image so that a positional axis of the superimposed image extends along the body axis direction.

10. The X-ray CT apparatus according to claim 1, wherein the value image includes an two axis graph, in which a first axis is the positional axis and a second axis is a value axis for the index value or the tube current value.

* * * * *